US008665071B2

(12) United States Patent
Morris et al.

(10) Patent No.: US 8,665,071 B2
(45) Date of Patent: *Mar. 4, 2014

(54) METHODS AND SYSTEMS FOR USING RFID IN BIOLOGICAL FIELD

(71) Applicant: Applied Biosystems, LLC, Carlsbad, CA (US)

(72) Inventors: Richard D. Morris, San Francisco, CA (US); Jerome A. Mack, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,267

(22) Filed: Nov. 29, 2012

(65) Prior Publication Data

US 2013/0088321 A1 Apr. 11, 2013

Related U.S. Application Data

(63) Continuation of application No. 13/615,070, filed on Sep. 13, 2012, which is a continuation of application No. 13/253,535, filed on Oct. 5, 2011, now Pat. No. 8,400,304, which is a continuation of application No. 13/014,366, filed on Jan. 26, 2011, now Pat. No. 8,049,623, which is a continuation of application No. 12/164,890, filed on Jun. 30, 2008, now Pat. No. 7,880,617, which is a continuation of application No. 11/647,065, filed on Dec. 28, 2006, now Pat. No. 7,663,487, which is a continuation of application No. 10/805,093, filed on Mar. 19, 2004, now Pat. No. 7,187,286.

(51) Int. Cl.
*H04Q 5/22* (2006.01)
*G06K 7/00* (2006.01)
*G06K 19/077* (2006.01)

(52) U.S. Cl.
CPC ........ *G06K 7/0008* (2013.01); *G06K 19/07749* (2013.01)
USPC .................... 340/10.1; 340/572.1; 340/572.8; 435/7.1

(58) Field of Classification Search
CPC .......... G06K 7/0008; G06K 19/07749; G01N 33/5438
USPC ......... 340/10.1, 572.1, 572.8, 572.7; 435/7.1; 436/47, 149, 155
See application file for complete search history.

(56) References Cited

U.S. PATENT DOCUMENTS

| 3,549,406 A | 12/1970 | Ambusk |
| 3,888,759 A | 6/1975 | Elson et al. |

(Continued)

FOREIGN PATENT DOCUMENTS

| DE | 3032069 | 6/1982 |
| DE | 3032071 | 7/1982 |

(Continued)

OTHER PUBLICATIONS

"Certified translation of JP 2001-188061", Jul. 2001.

(Continued)

*Primary Examiner* — John A Tweel, Jr.

(57) ABSTRACT

Biological reagent carrier devices and methods are disclosed, which employ RFID techniques to associate information with biological reagents.

20 Claims, 7 Drawing Sheets

(56) References Cited

U.S. PATENT DOCUMENTS

| | | |
|---|---|---|
| 3,960,499 A | 6/1976 | White |
| 4,006,069 A | 2/1977 | Hiratsuka et al. |
| 4,072,639 A | 2/1978 | Yamaguchi et al. |
| 4,094,759 A | 6/1978 | Ruhenstroth-Bauer et al. |
| 4,246,092 A | 1/1981 | Perry et al. |
| 4,411,490 A | 10/1983 | Daniel |
| 4,415,418 A | 11/1983 | Turre et al. |
| 4,415,428 A | 11/1983 | Nochumson et al. |
| 4,418,098 A | 11/1983 | Maistrovich |
| 4,548,869 A | 10/1985 | Ogawa et al. |
| 4,548,870 A | 10/1985 | Ogawa et al. |
| 4,569,794 A | 2/1986 | Smith et al. |
| 4,579,783 A | 4/1986 | Ogawa et al. |
| 4,600,641 A | 7/1986 | Ogawa et al. |
| 4,717,667 A | 1/1988 | Provonchee |
| 4,718,998 A | 1/1988 | Ogawa et al. |
| 4,737,259 A | 4/1988 | Ogawa et al. |
| 4,908,112 A | 3/1990 | Pace |
| 4,915,811 A | 4/1990 | Yamamoto et al. |
| 4,929,972 A | 5/1990 | Anderson et al. |
| 5,055,517 A | 10/1991 | Shorr et al. |
| 5,128,412 A | 7/1992 | Miyasaka et al. |
| 5,190,632 A | 3/1993 | Fujimiya et al. |
| 5,212,299 A | 5/1993 | Smith |
| 5,219,923 A | 6/1993 | Shorr |
| 5,225,212 A | 7/1993 | Martin et al. |
| 5,238,651 A | 8/1993 | Chuba |
| 5,252,294 A | 10/1993 | Kroy et al. |
| 5,306,468 A | 4/1994 | Anderson et al. |
| 5,384,028 A | 1/1995 | Ito |
| 5,395,619 A | 3/1995 | Zalipsky et al. |
| 5,397,449 A | 3/1995 | Zewert et al. |
| 5,455,344 A | 10/1995 | Harper et al. |
| 5,476,016 A | 12/1995 | Fedorka-Cray et al. |
| 5,498,324 A | 3/1996 | Yeung et al. |
| 5,585,069 A | 12/1996 | Zanzucchi et al. |
| 5,641,400 A | 6/1997 | Kaltenbach et al. |
| 5,641,626 A | 6/1997 | Dumais et al. |
| 5,641,634 A | 6/1997 | Mandecki |
| 5,670,226 A | 9/1997 | Yoshizawa et al. |
| 5,672,416 A | 9/1997 | Radola et al. |
| 5,681,437 A | 10/1997 | Black et al. |
| 5,700,429 A | 12/1997 | Buhler et al. |
| 5,741,462 A | 4/1998 | Nova et al. |
| 5,751,629 A | 5/1998 | Nova et al. |
| 5,764,892 A | 6/1998 | Cain et al. |
| 5,770,455 A | 6/1998 | Cargill et al. |
| 5,779,868 A | 7/1998 | Parce et al. |
| 5,790,727 A | 8/1998 | Dhadwal et al. |
| 5,817,472 A | 10/1998 | Hardham et al. |
| 5,840,877 A | 11/1998 | Kozulic |
| 5,851,370 A | 12/1998 | Maracas et al. |
| 5,851,488 A | 12/1998 | Saul et al. |
| 5,859,587 A | 1/1999 | Alicot et al. |
| 5,874,214 A | 2/1999 | Nova et al. |
| 5,882,679 A | 3/1999 | Needham |
| 5,883,376 A | 3/1999 | Rosch et al. |
| 5,885,432 A | 3/1999 | Hooper et al. |
| 5,910,287 A | 6/1999 | Cassin et al. |
| 5,925,562 A | 7/1999 | Nova et al. |
| 5,949,049 A | 9/1999 | McCarrick et al. |
| 5,953,682 A | 9/1999 | McCarrick et al. |
| 5,954,931 A | 9/1999 | Maracas et al. |
| 5,962,834 A | 10/1999 | Markman |
| 5,990,238 A | 11/1999 | DiZio et al. |
| 5,993,627 A | 11/1999 | Anderson et al. |
| 6,013,168 A | 1/2000 | Arai |
| 6,017,624 A | 1/2000 | Delgado et al. |
| 6,025,129 A | 2/2000 | Nova et al. |
| 6,025,159 A | 2/2000 | Nova |
| 6,027,695 A | 2/2000 | Oldenburg et al. |
| 6,031,458 A | 2/2000 | Jacobsen et al. |
| 6,060,022 A | 5/2000 | Pang et al. |
| 6,071,394 A | 6/2000 | Cheng |
| 6,085,603 A | 7/2000 | Riekkinen |
| 6,090,251 A | 7/2000 | Sundberg et al. |
| 6,090,255 A | 7/2000 | Riley et al. |
| 6,094,137 A | 7/2000 | Rasch et al. |
| 6,103,199 A | 8/2000 | Bjornson et al. |
| 6,112,152 A | 8/2000 | Tuttle |
| 6,123,821 A | 9/2000 | Anderson et al. |
| 6,132,685 A | 10/2000 | Kercso et al. |
| 6,136,173 A | 10/2000 | Anderson et al. |
| 6,139,709 A | 10/2000 | Scott |
| 6,140,146 A | 10/2000 | Brady et al. |
| 6,147,662 A | 11/2000 | Grabau |
| 6,171,780 B1 | 1/2001 | Pham et al. |
| 6,187,250 B1 | 2/2001 | Champagne |
| 6,201,474 B1 | 3/2001 | Brady et al. |
| 6,206,292 B1 | 3/2001 | Robertz et al. |
| 6,211,781 B1 | 4/2001 | McDonald |
| 6,219,137 B1 | 4/2001 | Vo-Dinh |
| 6,245,206 B1 | 6/2001 | Anderson et al. |
| 6,251,516 B1 | 6/2001 | Bonner et al. |
| 6,258,606 B1 | 7/2001 | Kovacs |
| 6,259,367 B1 | 7/2001 | Klein |
| 6,277,630 B1 | 8/2001 | Brophy et al. |
| 6,278,794 B1 | 8/2001 | Parekh et al. |
| 6,280,590 B1 | 8/2001 | Cheng |
| 6,297,727 B1 | 10/2001 | Nelson, Jr. |
| 6,300,141 B1 | 10/2001 | Segal et al. |
| 6,317,028 B1 | 11/2001 | Valiulis |
| 6,317,208 B1 | 11/2001 | Hirosawa |
| 6,319,668 B1 | 11/2001 | Nova et al. |
| 6,329,139 B1 | 12/2001 | Nova et al. |
| 6,352,854 B1 | 3/2002 | Nova et al. |
| 6,359,444 B1 | 3/2002 | Grimes |
| 6,361,950 B1 | 3/2002 | Mandecki |
| 6,372,428 B1 | 4/2002 | Nova et al. |
| 6,376,187 B1 | 4/2002 | Mandecki |
| 6,387,623 B1 | 5/2002 | Mandecki |
| 6,416,714 B1 | 7/2002 | Nova et al. |
| 6,417,010 B1 | 7/2002 | Cargil et al. |
| 6,429,016 B1 | 8/2002 | McNeil |
| 6,454,924 B2 | 9/2002 | Jedrzejewski et al. |
| 6,458,259 B1 | 10/2002 | Parce et al. |
| 6,483,434 B1 | 11/2002 | UmiKer |
| 6,520,544 B1 | 2/2003 | Mitchell et al. |
| 6,521,111 B1 | 2/2003 | Amshey et al. |
| 6,535,129 B1 | 3/2003 | Petrick |
| 6,541,211 B1 | 4/2003 | Patek et al. |
| 6,586,143 B1 | 7/2003 | Tan |
| 6,637,473 B2 | 10/2003 | Ganz et al. |
| 6,652,812 B1 | 11/2003 | Vartiainen |
| 6,670,609 B2 | 12/2003 | Franzen et al. |
| 6,677,852 B1 | 1/2004 | Landt |
| 6,686,158 B2 | 2/2004 | Mandecki |
| 6,699,437 B1 | 3/2004 | Astle |
| 6,726,820 B1 | 4/2004 | Frazier |
| 6,733,728 B1 | 5/2004 | Mimura et al. |
| 6,734,797 B2 | 5/2004 | Shanks et al. |
| 6,806,050 B2 | 10/2004 | Zhou |
| 6,824,738 B1 | 11/2004 | Neeper et al. |
| 6,824,740 B1 | 11/2004 | Sheldon, III et al. |
| 6,847,912 B2 | 1/2005 | Forster |
| 6,858,439 B1 | 2/2005 | Xu |
| 6,867,048 B2 | 3/2005 | Kovacs |
| 6,881,314 B1 | 4/2005 | Wang et al. |
| 6,887,362 B2 | 5/2005 | Huang et al. |
| 6,889,468 B2 | 5/2005 | Bedingham et al. |
| 6,906,797 B1 | 6/2005 | Kao et al. |
| 6,917,291 B2 | 7/2005 | Allen |
| 6,928,353 B2 | 8/2005 | Finley et al. |
| 6,934,836 B2 | 8/2005 | Strand et al. |
| 6,935,560 B2 | 8/2005 | Andreasson et al. |
| 6,942,778 B1 | 9/2005 | Jalali |
| 6,953,834 B2 | 10/2005 | Dejong |
| 6,982,640 B2 | 1/2006 | Lindsay et al. |
| 6,986,836 B2 | 1/2006 | Panattoni et al. |
| 7,053,777 B2 | 5/2006 | Allen |
| 7,061,379 B2 | 6/2006 | Chen et al. |
| 7,091,864 B2 | 8/2006 | Veitch et al. |
| 7,113,131 B2 | 9/2006 | Burke |
| 7,118,708 B2 | 10/2006 | Mordekhay |

(56) References Cited

U.S. PATENT DOCUMENTS

| | | |
|---|---|---|
| 7,142,987 B2 | 11/2006 | Eggers |
| 7,153,403 B2 | 12/2006 | Alpenfels et al. |
| 7,187,286 B2 | 3/2007 | Morris et al. |
| 7,298,885 B2 | 11/2007 | Green et al. |
| 7,338,811 B2 | 3/2008 | Lai |
| 7,361,260 B2 | 4/2008 | Amshey et al. |
| 7,382,258 B2 | 6/2008 | Oldham et al. |
| 7,390,458 B2 | 6/2008 | Burow et al. |
| 7,663,487 B2 | 2/2010 | Morris et al. |
| 7,880,617 B2 | 2/2011 | Morris et al. |
| 8,049,623 B2 | 11/2011 | Morris et al. |
| 8,059,623 B2 | 11/2011 | Gandham et al. |
| 8,400,304 B2 * | 3/2013 | Morris et al. ............. 340/572.1 |
| 2001/0008390 A1 | 7/2001 | Berquist et al. |
| 2001/0021356 A1 | 9/2001 | Konrad |
| 2002/0018733 A1 | 2/2002 | Kapplein et al. |
| 2002/0030598 A1 | 3/2002 | Dombrowski et al. |
| 2002/0052238 A1 | 5/2002 | Muroi |
| 2002/0076819 A1 | 6/2002 | Bowman et al. |
| 2002/0077886 A1 | 6/2002 | Chung |
| 2002/0090320 A1 | 7/2002 | Burow et al. |
| 2002/0094515 A1 | 7/2002 | Erlach et al. |
| 2002/0098472 A1 | 7/2002 | Erlach et al. |
| 2002/0098598 A1 | 7/2002 | Coffen et al. |
| 2002/0111551 A1 | 8/2002 | Erlach et al. |
| 2002/0114739 A1 | 8/2002 | Weigl et al. |
| 2003/0017082 A1 | 1/2003 | Van Deursen et al. |
| 2003/0058110 A1 | 3/2003 | Rich |
| 2003/0072676 A1 | 4/2003 | Fletcher-Haynes et al. |
| 2003/0087446 A1 | 5/2003 | Eggers et al. |
| 2003/0087455 A1 | 5/2003 | Eggers et al. |
| 2003/0087955 A1 | 5/2003 | Miller et al. |
| 2003/0124539 A1 | 7/2003 | Warrington et al. |
| 2003/0151028 A1 | 8/2003 | Lawrence et al. |
| 2003/0183683 A1 | 10/2003 | Stewart |
| 2003/0190608 A1 | 10/2003 | Blackburn |
| 2003/0196897 A1 | 10/2003 | Alpenfels et al. |
| 2003/0211012 A1 | 11/2003 | Bergstrom et al. |
| 2003/0217925 A1 | 11/2003 | Alpenfels et al. |
| 2003/0231986 A1 | 12/2003 | Kocher |
| 2004/0029109 A1 | 2/2004 | Lai |
| 2004/0029310 A1 | 2/2004 | Bernds et al. |
| 2004/0094949 A1 | 5/2004 | Savagian et al. |
| 2004/0100380 A1 | 5/2004 | Lindsay et al. |
| 2004/0100415 A1 | 5/2004 | Veitch et al. |
| 2004/0101966 A1 | 5/2004 | Davis et al. |
| 2004/0121432 A1 | 6/2004 | Klein et al. |
| 2004/0124437 A1 | 7/2004 | Doudoumopolous |
| 2004/0131505 A1 | 7/2004 | Koeda |
| 2004/0133092 A1 | 7/2004 | Kain |
| 2004/0136873 A1 | 7/2004 | Meier |
| 2004/0155754 A1 | 8/2004 | Fischer et al. |
| 2004/0161795 A1 | 8/2004 | Marto |
| 2004/0172160 A1 | 9/2004 | O'Dougherty et al. |
| 2004/0173508 A1 | 9/2004 | Deursen et al. |
| 2004/0173781 A1 | 9/2004 | Lawrence et al. |
| 2004/0175515 A1 | 9/2004 | Lawrence et al. |
| 2004/0175548 A1 | 9/2004 | Lawrence et al. |
| 2004/0175550 A1 | 9/2004 | Lawrence et al. |
| 2004/0193449 A1 | 9/2004 | Wildman et al. |
| 2004/0195102 A1 | 10/2004 | Panattoni et al. |
| 2004/0202577 A1 | 10/2004 | McNeil et al. |
| 2004/0203047 A1 | 10/2004 | Caren et al. |
| 2004/0222297 A1 | 11/2004 | Dearing et al. |
| 2005/0159982 A1 | 7/2005 | Showalter et al. |
| 2005/0205673 A1 | 9/2005 | Morris et al. |
| 2005/0219039 A1 | 10/2005 | Allen |
| 2005/0242963 A1 * | 11/2005 | Oldham et al. ............. 340/572.8 |
| 2005/0276728 A1 | 12/2005 | Muller-Cohn |
| 2006/0099567 A1 | 5/2006 | Muller-Cohn |
| 2006/0173750 A1 | 8/2006 | Naley |
| 2006/0190185 A1 | 8/2006 | Ford et al. |
| 2006/0199196 A1 | 9/2006 | O'Banion et al. |
| 2006/0283945 A1 | 12/2006 | Excoffier et al. |
| 2007/0120685 A1 * | 5/2007 | Morris et al. ............. 340/572.8 |
| 2008/0235055 A1 | 9/2008 | Mattingly et al. |
| 2008/0237043 A1 | 10/2008 | Amshey et al. |
| 2008/0238627 A1 * | 10/2008 | Oldham et al. ............. 340/10.1 |
| 2008/0284602 A1 * | 11/2008 | Morris et al. ............. 340/572.1 |
| 2009/0071829 A1 | 3/2009 | O'Banion et al. |
| 2010/0307921 A1 | 12/2010 | Frazier |
| 2011/0001609 A1 * | 1/2011 | Oldham et al. ............. 340/10.1 |
| 2011/0115633 A1 * | 5/2011 | Morris et al. ............. 340/572.8 |
| 2012/0145798 A1 | 6/2012 | Morris et al. |
| 2013/0063252 A1 * | 3/2013 | Morris et al. ............. 340/10.1 |

FOREIGN PATENT DOCUMENTS

| | | |
|---|---|---|
| DE | 3032070 | 10/1982 |
| EP | 0376611 | 7/1990 |
| JP | 2001257255 | 10/1989 |
| JP | 2009111198 | 4/1997 |
| JP | 2001-188061 | 7/2001 |
| JP | 2003-289566 | 10/2003 |
| JP | 2004-61136 | 2/2004 |
| JP | 2004-93519 | 3/2004 |
| JP | 2004-166555 | 6/2004 |
| JP | 2004246492 | 9/2004 |
| JP | 11511238 | 1/2009 |
| WO | WO-9608433 | 3/1996 |
| WO | WO-96/36436 | 11/1996 |
| WO | WO9859092 | 4/1998 |
| WO | WO0147638 | 7/2001 |
| WO | WO2005040500 | 5/2005 |
| WO | WO-2005/113147 | 12/2005 |
| WO | WO-2006/060125 | 6/2006 |

OTHER PUBLICATIONS

"Investor's Relationship,", Vincogen web page downloaded from http://www.vincogen.com/Investor/.htm, Jan. 29, 2004.
"New RFID Tag with More Memory", *RFID Journal*, Aug. 25, 2003.
"Report: RFID Labels", Williams Inference Center, vol. 27, No. 15, Sep. 28, 2000.
"RFID Radio Frequency Identification FRID, A basic primer, the Association of the Automatic Identification and Data Capture Industry", AIM, Inc., Pittsburgh, Pennsylvania, USA., Aug. 23, 2001, 1-17.
"Technology", Vincogen web page downloaded from http://www.vincogen.com/technologyl.htm, Jan. 29, 2004.
"The Write Stuff: Understanding the Value of Read/Write RFID Functionality, White Paper", Intermec Technologies Corporation, USA, 2003.
Henke, Cliff, "DNA-chip technologies Part 1: Research fundamentals and inudstry catalysts", *IVD Technology Magazine*, 1998.
Henke, Cliff, "DNA-chip technologies Part 2: State-of-the-art and competing technologies", *IVD Technology Magazine*, 1998.
Henke, Cliff, "DNA-chip technologies Part 3: What does the future hold?", *IVD Technology Magazine*, 1998.
Kambil, Ajit, "Move Over Barcodes; Consumer-Goods Firms Eye Radio-Frequency ID", *A Deloitte Research Engineering Technologies Brief*, Deloitte Consulting, 2003, 1-5.
Kuchinskas, Susan , "IP Addresses for Coke Cans", earthwebnews.com, Sep. 5, 2003.
Moran, Edmund et al., "Radio Frequency Tag Encoded Combinatorial Library Method for the Discovery of Tripeptide-Substituted Cinnamic Acid Inhibitors of the Protein Tyrosine Phosphatase PTP1B", *J. Am. Chem. Soc.*, vol. 117, 1995, 10787-10788.
Pharmaseq, "Illustration of a Microtransponder for DNA-Prob Assays", Pharmaseq web page downloaded from http://www.pharmaseq.com/illustration.html, Sep. 23, 2004.
Service, Robert, "Radio Tags Speed Compound Synthesis", *Science*, vol. 270, Oct. 27, 1995, 577.
Zebra Technologies, "RFID: The Next Generation of AIDC", Application White Paper, Aug. 2004, 1-13.
Zebra Technologies, "Zebra's RFID Readiness Guide: Complying with RFID Tagging Mandates", Application White Paper, Jan. 2004, 1-9.
"Investor's Relationship," Vincogen web page downloaded from http://www.vincogen.com/Investor/.htm, Jan. 29, 2004.

(56) References Cited

OTHER PUBLICATIONS

Kambil, Ajit, "Move Over Barcodes; Consumer-Goods Firms Eye Radio-Frequency ID", *A Deloitte Research Engineering Technologies Brief*, Deloitte Consulting, 2003, 1-5.
Kuchinskas, Susan, "IP Addresses for Coke Cans", earthwebnews. com, Sep. 5, 2003.
Ausubel, F.M. et al. "Current Protocols in Molecular Biology", Supplement 63, (Table of Contents), 1998.
Baines, M.G. et al. "Purification of Immunoglobulin G (IgG)" Meth. Molec. Biol., Vo. 10, 1992, pp. 79-104.
Barbas, et al. "A companion to Methods in Immunology" Methods, vol. 2, 1991, p. 119.
Birge, R. et al. "Biomolecular Electronics: Protein-Based Associative Processors and Volumetric Memories", J. Phys. Chem B., B, 103, 1999, pp. 10746-10766.
Birge, R., "Protein-Based Three Dimensional Memory—A light-absorbing molecule from bacteria could provide faster access time and denser data storage in three-dimensional optical memories", American Scientist, vol. 82, 1994, pp. 348-355.
Brush, M., "Prepare to Cast Off: A Profile of Precast Acrylamide Gels", The Scientist, vol. 12, No. 15, 1998, pp. 1-9.
Cooper, H. et al. "Production of Antibodies", Current Protocols in Immunology, Section II, Unit 2.4, Supplement 13, 1995, Sections 2.4.1-2.4.9.
Ecker, et al. "Combinatorial drug discovery: which methods will produce the greatest value?", Biotechnology, 13, 1990, pp. 351-360.
EP Patent App # EP01931132.3 Supplemental European Search Report mailed Aug. 14, 2008.
EP Patent App # EP05851446 Supplementary European Search Report dated Mar. 15, 2012.
Flotte Prospects for virus-based gene dierapy for. cysticfibrosis./ Bioenerg Biomembr., J. Bioenerg. Biomemb., 92, 1993, pp. 381-387.
Fraley, R. et al. "New generation liposomes: the engineering of an efficient vehicle for intracellular delivery of nucleic acids" Trends Biochem Sci., vol. 6, 1981, pp. 77-80.
Frost, P., "Tiny Channels Carved in Plastic Enable Medical Test on a CD", Ohio State Research News, 2000.
GelBondÂ® film downloaded from http://www.bioproducts.com/ product. Mar. 27, 2000.
GelBondAÂ® PAG film downloaded from http://www.bioproducts. com/product . . . Mar. 27, 2000.
Goeddel, Gene Expression Technology, Meth. Enzymol., vol. 185, 1990.
Green, J. et al. "Production of Polyclonal Antisera", Immunochemical Protocols, Methods in Molecular Biology, vol. 10, 1992, 1-5.
Green, L. et al. "Antigen-specific human monoclonal antibodies from mice engineered with human Ig heavy and light chain YACs", Nature Genetics, vol. 7, 1994, pp. 13-21.
Gregoriadis, G., "Liposome Technology: Preparation of Liposomes", CFC Press NY, 1984, Table of Contents only.
Harlow, E. et al. Antibodies: A Laboratory Manual, Cold Spring Harbor Laboratory Press, 2nd Edition, 1988, pp. 116-120.
http://www.dupont.com/industrial-polymers/nucrel/, Apr. 17, 2008.
Huse, W. D. et al. "Generation of a large combinatorial library of the immunoglobulin repertoire in phage lambda", Science, vol. 246, 1989, pp. 1275-1281.
Jellinek, et al. "Potent 2'-Amino-2'-Deoxypyrimidine RNA Inhibitors of Basic Fibroblast Growth Factor.", Biochemistry, 34, 1995, pp. 11363-11372.
Jolly, et al. "Viral vector systems for gene therapy", Canc. Gene Therapy vol. 1, 1994, pp. 51-64.
Köhler, G. et al. "Continuous cultures of fused cells secreting antibody of predefined specificity", Nature, vol. 256, Aug. 7, 1975, pp. 495-497.
Lee, Y., "Applications Note AN710, Antenna Circuit Design for RFID Applications", Microchip Technology, Inc., 2003.
Lin, Yun et al. "Modified RNA sequence pools for in vitro selection", Nucleic Acids Research, vol. 22, No. 24, 1994, pp. 5220-5234.
Lonberg, et al. "Antigen-specific human antibodies from mice comprising four distinct genetic modifications", Nature, 368, 1994, pp. 856-859.
Membrane Filters downloaded from http://www.voigtglobal.com/ membfil.htm Apr. 6, 2000.
Michael, S. et al. "Binding-incompetent Adenovirus Facilitates Molecular Conjugate-mediated Gene Transfer by the Receptor-mediated Endocytosis Pathway", The Journal of Biological Chemistry, 268, 1993, 6866-6869.
Morishita, et al. "Novel and Effective Gene Transfer Technique for Study of Vascular Renin Angiotensin System", J. Clin. Invest., 91, 1993, pp. 2580-2585.
Pagratis, et al. "Potent 2'-amino-, and 2'-fluoro-2'-deoxyribonucleotide RNA inhibitors of keratinocyte growth factor", Nature Biotechnology, vol. 15, 1997, pp. 68-73.
PCT/US01/40489 International Search Report mailed Jul. 6, 2001.
PCT/US05/40500 International Preliminary Report on Patentability mailed Jul. 19, 2007.
PCT/US05/40500 International Search Report and Written Opinion mailed May 30, 2007.
Polycarbonate Membrane Filters downloaded from http://www.2spi. com/catalog/spec_prep/filter3.html, Apr. 6, 2000.
Sambrook, et al. "Ch: 16.30-16.60—Introduction of Recombinant Vectors into Mammalian Cells", Molecular Cloning, a Laboratory Manual, 2nd ed., Cold Spring Harbor Laboratory Press, Cold Spring Harbor, NY, 1989, pp. 16.30-16.60.
Tam, et al. "Biological availability and nuclease resistance extend the in vitro activity of a phosphoraothioate-3'hydroxypropylamine", Nucleic Acids Research, vol. 22, 1994, pp. 977-986.
Taylor, et al. "Human immunoglobulin transgenes undergo rearrangement, somatic mutation and class switching in mice that lack endogenous IgM", International Immunology, vol. 6, 1994, 579-591.
Ward, et al. "Binding activities of a repertoire of single immunoglobulin variable domains secreted from *Escherichia coli*", Nature, 341, 1989, pp. 544-546.
Winter, et al. "Humanized antibodies.", Immunol. Today, 14, 1993, pp. 243-246.
Winter, et al. "Making antibodies by phage display technology.", Annu. Rev. Immunol, 12, 1994, pp. 433-455.
US 7,165,720, 01/2007, Linton et al. (withdrawn)

* cited by examiner

METHODS AND SYSTEMS FOR USING RFID IN BIOLOGICAL FIELD

INTRODUCTION

The present teaching relates to methods and systems for associating information with carriers for supporting biological reagents. During the manufacture and use of biological reagents, the reagents are typically coded and labeled in order to keep track of them. Conventional systems use bar codes to identify carriers containing reagents to be processed by analytical instrumentation. Bar codes, however, require printing and application of a bar code label to carriers for the biological reagents. At some later time the bar code is read by either a hand-held bar code scanner or by an automated bar-code scanner controlled by the instrumentation to track the reagents as they are processed.

To read a label or a barcode, however, requires an optical path to the barcode, which can be inconvenient and problematic, for example if the indicia to be read are located inside of an instrument. In the past these problems have been addressed by forming windows in the instruments or carriers to provide an optical path to the labels. Such windows can complicate the design of instruments and carriers and depending on the configuration and design of a particular window, the optical path can be distorted, resulting in optical reading and scanning problems. Further reading problems can result from printing inconsistencies and any material that covers the bar code, such as frost in a refrigerator.

Further, if information needs to be added to a label associated with a particular sample, physical access is required to print the additional information to the label. Moreover, only a limited amount of information, can be printed on a label associated with a carrier due to label space limitations. When using bar codes, 1-D and 2-D bar codes are limited as to how much information can be printed in a given amount of space by the visual resolution between marks. Therefore, typically a printed carrier number or identifier is used as an index into a database of information regarding the carrier or the contents of the carrier. The database was typically provided on a separate CDROM or other removable machine-readable medium. However, it can be inconvenient to associate the information on particular CDROM with a particular carrier.

Vincogen Corporation of Trevose, Pa. purports to have filed U.S. patent application Ser. No. 10/396,269, on using RFID technology in connection with biochips to provide an identifier number for such biochips. However, the Vincogen product fails to address the above-identified deficiencies of existing methods and systems.

Accordingly, systems and methods are needed that provide for the reading from and writing to carriers for biological reagents without requiring an optical path or direct physical access to the carriers. Moreover, there is need for storing greater amounts of information than can be written on a conventional label. SUMMARY According to various embodiments, apparatus is provided for associating information with a biological reagent according to the present teachings. The apparatus can include a carrier for supporting the biological reagent and at least one RFID tag including a carrier RFID antenna coupled to the carrier, wherein the RFID tag is operable to be read by an RFID reader, and the RFID tag can include identification, supplemental, and/or rights information for the biological reagent.

According to various embodiments, apparatus is provided for associating information with a microarray according to the present teachings. The apparatus can include a substrate; at least one chamber coupled to the microarray; and an RFID tag having an RFID antenna coupled to the substrate.

According to various embodiments, apparatus is provided for associating information with a biological reagent according to the present teachings. The apparatus can include a carrier for the biological reagent. The carrier is coupled to an RFID tag, and the RFID tag is operable to be read by an RFID reader. The RFID tag contains identification information. Further, an instrument is provided for reading the identification information, and performing operations on the biological reagent, the instrument including an output for providing an identity indication of the biological reagent based on the identification information. The instrument is generally opaque and blocks optical paths to contents of the instrument.

According to various embodiments, the present teachings involve methods for associating information regarding biological reagents with carriers for supporting the biological reagents. A carrier for the biological reagents is provided, and the carrier is coupled to an RFID tag so that the RFID tag can be read by an RFID reader. Identification, supplemental, and/or, rights information associated with the biological reagent is received from the RFID tag.

According to various embodiments, apparatus for associating information with a biological reagent is provided. The apparatus includes a carrier for supporting the biological reagent and an RFID tag including a carrier RFID antenna coupled to the carrier. The RFID tag can be read by an RFID reader, and the RFID tag includes instrument operation information for the biological reagent.

According to various embodiments, a method for associating information regarding operations for biological reagents with carriers for supporting the biological reagents is provided. The method includes providing a carrier for at least one biological reagent, the carrier coupled to an RFID tag, which can be read by an RFID reader. The method also includes receiving, from the RFID tag, instrument operation information associated with the biological reagent.

It is understood that both the foregoing general description and the following description of various embodiments are exemplary and explanatory only and are not meant to be restrictive or to be read into the claims. The accompanying drawings, which are incorporated in and constitute a part of this specification, illustrate some embodiments, and together with the description serve to explain the principles of the embodiments described herein.

BRIEF DESCRIPTION OF THE DRAWINGS

The skilled artisan will understand that the drawings, described below, are only intended for the illustration of various embodiments. The drawings are not intended to limit the scope of the present teachings in any way.

DESCRIPTION OF VARIOUS EMBODIMENTS

Figure 1:
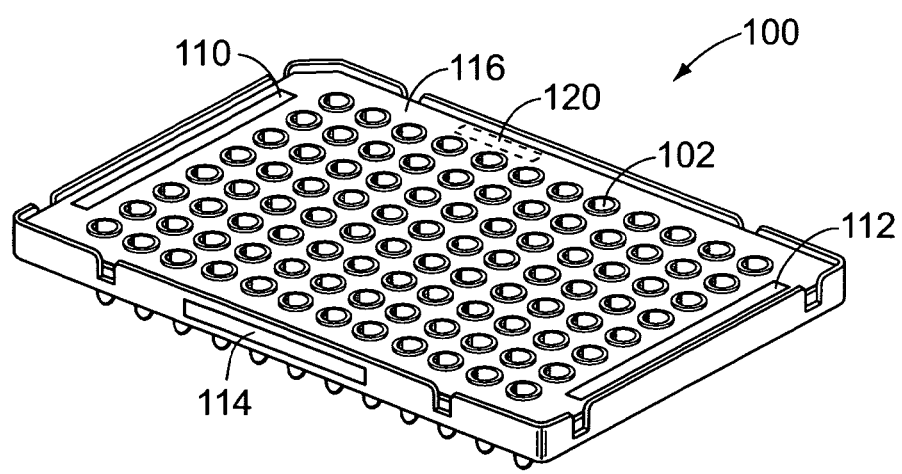
FIG. 1 illustrates a perspective view from above a reaction plate having a plurality of reaction wells and various exemplary locations for RFID tags according to various embodiments.

Reference will now be made in detail to some embodiments, examples of which are illustrated in the accompanying drawings. Wherever possible, the same reference numbers are used throughout the drawings to refer to the same or like parts.

Radio Frequency Identification ("RFID") provides a convenient mechanism for identifying and detecting objects using wireless electro-magnetic signals. A basic RFID system has at least one RFID reader and at least one RFID tag. Typically, RFID readers can include a coil or antenna and circuitry to transmit and receive signals with the coil or antenna. An RFID tag also includes a coil or antenna and some information that can be read by an RFID reader.

The RFID reader antenna generates an electromagnetic field, thereby transferring energy to the tag. Depending on the design of the tag, a portion of the energy transferred to the tag will be reflected to the reader so as to provide information about the tag back to the reader. Some RFID systems can be used to read and optionally write data to and from the RFID tag. RFID readers can generate signals spanning distances from less than one inch to more than 100 feet depending on frequency and power of the signals generated at the RFID reader antenna.

Typically, RFID tags are categorized as either active or passive. Active RFID tags are powered by an internal battery and are typically read/write, i.e., tag data can be rewritten and/or modified. An active tag's memory size varies according to application requirements; some systems operate with up to 1 MB of memory.

Passive RFID tags operate without a separate external power source and obtain operating power generated from the reader. Passive tags are consequently typically lighter than active tags, less expensive, and offer a long operational lifetime. Passive tags typically have shorter read ranges than active tags and require a higher-powered reader. Read-only tags are typically passive and can be programmed with a unique set of data (usually 32 to 128 bits) that is typically predetermined at the time of manufacture of the tag. It is understood that passive read/write tags can also be employed consistent with the present teachings.

The term "RFID tag" as used herein refers to either an active or passive RFID tag that contains information. The RFID tag can be read only or read/write, and the information associated with the RFID tag can be hard-coded into the RFID tag at the time of manufacture or at some later time, or the RFID tag can contain information that is written to the RFID tag throughout its lifetime.

The term "RFID reader" as used herein includes RFID devices that can read information from and/or write information into an RFID tag.

The term "carrier" as used herein refers to a structure for directly or indirectly supporting a biological reagent. Examples of carriers include reaction plates, tubes, tube carriers, surface plasmon resonance arrays, slides, conical low-volume tubes, microfluidic cards, microarray cartridges, microarrays, and other types of containers for supporting biological reagents.

The term "biological reagent" as used herein refers to a biological material used for various biological analyses such as detecting, examining, and/or measuring information from biological samples. Biological analyses can include reactions such as polymerase chain reaction (PCR), ligase chain reaction, antibody binding reaction, oligonucleotide ligation assays, and hybridization assays. Examples of biological reagents include nucleic acids, primers, probes, and other biological reagents, which can be used in performing various biological assays. "Nucleic acid" as used herein refers to nucleotides, oligonucleotides, DNA, RNA, PNA, etc. as these terms are understood by those skilled in the art of genomics.

The term "information" as used herein refers to data that can be stored electronically in the RFID tag and can be retrieved to be used as machine readable or human readable data for processing the biological reagent and/or carrier.

The term "identification information" as used herein refers to information on an RFID tag that can be used to uniquely identify a particular carrier or biological reagent or to distinguish the carrier or biological reagent from other carriers or biological reagents. For example, identification can relate a particular assay prepared for a particular customer.

The term "supplemental information" as used herein refers to descriptive information about a carrier or its contents, including certain biological reagents. Examples of supplemental information include nucleic acid sequence information and annotated information regarding experiments performed with various biological reagents.

The term "rights information" as used herein refers to authorization information for carriers or biological reagents, such as information regarding whether a particular licensee has a valid license to use a particular carrier or biological reagent, including a number of times the licensee is permitted to use the particular carrier or biological reagent in a particular assay. Rights information can also include validation information regarding whether a particular carrier or biological reagent has been subject to a recall or has otherwise become unsuitable or unauthorized for use.

The term "genealogy information" as used herein refers to information regarding the derivation of a biological reagent, including for example an identification of an original sample from which it was derived or the number of generations removed it is from an original sample.

The term "traveler information" as used herein refers to information regarding a carrier or a biological reagent contained as operations are performed on that carrier or biological reagent for example during manufacture of the biological reagent or while an assay is being performed on the biological reagent.

Figure 7:
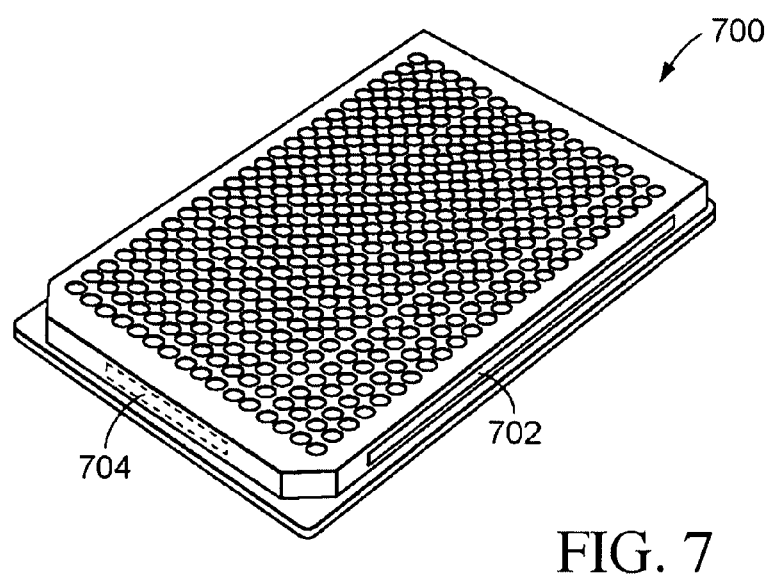
FIG. 7 illustrates another exemplary embodiment of a reaction plate in connection with various exemplary locations for RFID tags according to various embodiments.

FIG. 1 illustrates a perspective view from above of a reaction plate 100 having a plurality of reaction wells 102 and exemplary locations 110, 112, 114, and 120 for RFID tags. It is understood that exemplary location 110 for the RFID tag, for example, can be positioned on the exterior of the reaction plate 100 in any convenient location that will permit appropriate antenna geometry and accommodate the necessary passive or active RFID circuitry necessary for proper operation of the RFID tag. For example, RFID tags 110 and 112 are shown as boxes placed in the margins of the reaction plate 110 on an upper surface 116 of the reaction plate 100. Adhesive application of an RFID tag to the surface 116 of the reaction plate 100 can advantageously permit standard consumables, such as reaction plate 100 to be manufactured and/or acquired independently from the RFID tags. Alternatively, RFID tag 120, illustrated in broken lines, can be embedded in the reaction plate 100, for example during a plastic injection molding or a blow molding manufacturing process. Trays and microcards are typically constructed of polypropylene so as to be compatible with PCR thermal cycling. Other carriers that provide transport containers as opposed to reaction containers can be made of harder plastics e.g. Lexan® (General Electric). FIG. 1 illustrates a 96-well reaction plate. As illustrated in FIG. 7, other reaction plates such as 386-well reaction plates are contemplated by the present teachings.

Figure 2:
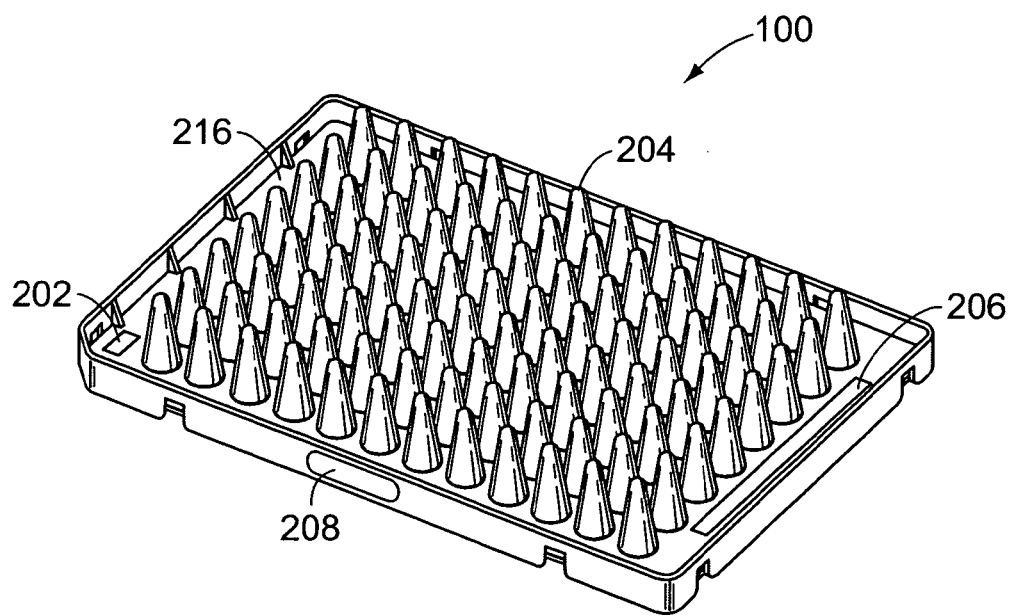
FIG. 2 illustrates a perspective view from beneath a reaction plate having a plurality of reaction wells and various exemplary locations for RFID tags according to various embodiments.

FIG. 2 illustrates an underside perspective view of the reaction plate 100 showing the undersides 204 of a plurality of reaction wells and at least one RFID tag 202 affixed to an underside portion of the reaction plate. As shown in FIG. 2, the RFID tags can be placed on the underside of the carrier as shown in connection with RFID tags 202 and 206, which are shown to be applied to the surface 216 of the reaction plate 100. Alternatively, an RFID tag 208 can be applied to a side surface of the reaction plate 100. As set forth in connection with FIG. 1, in various embodiments, the RFID tags can, for example, be adhesively applied to consumables, such as on the reaction plate 100. However, the RFID tags can also be embedded in the body of the consumables, for example during a plastic injection molding or a blow molding manufacturing process. To facilitate a transition from barcodes to RFID, both barcodes (not shown) and RFID tags can be present on consumables consistent with the present teachings, such as the reaction plate 100.

According to various embodiments, the reaction plates contain biological reagents such as nucleic acid materials, primers, and probes, which are used in connection with various biological assays to determine, for example a genetic sequence of a particular sample. In various embodiments, separate RFID tags on the plate are associated with groups of wells within the reaction plate. In other embodiments, an RFID tag is associated with a single well in the reaction plate 100. In other embodiments, a single RFID tag is associated with the entire reaction plate, with the RFID tag containing information regarding each of the wells and the contents and history of the contents of each of the well. In such embodiments, a read/write RFID tag containing a substantial amount of memory can include, for example, identification, supplemental, and/or rights information about the contents of the wells 102 (of FIG. 1).

Figure 3:
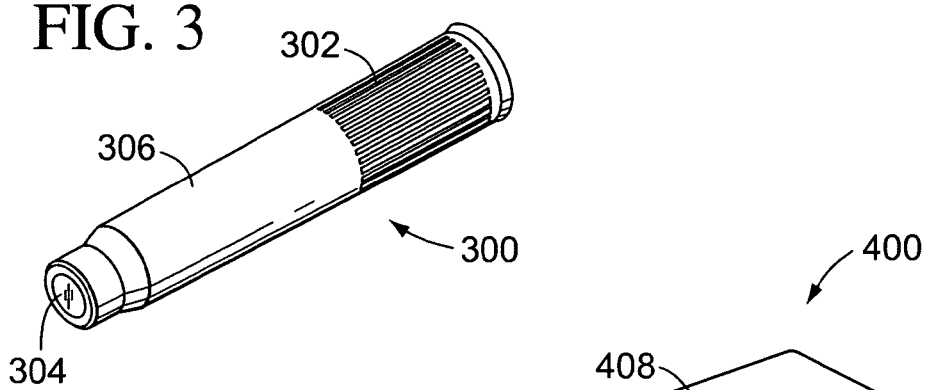
FIG. 3 illustrates a tube in connection with various exemplary locations for RFID tags according to various embodiments.

FIG. 3 illustrates a tube 300 having RFID tags positioned in alternative configurations on the tube 300. The tubes can have a conical internal volume to provide pipette access to small volumes. In various embodiments, the tubes bear both human-readable and/or machine-readable indicia regarding the contents of the tube and/or barcodes in addition to an RFID tag. In various embodiments, the RFID tag is adhesively applied to outer surface 306 of the tube 300 in connection with a label for providing optically-accessible indicia. In various embodiments, RFID tags are provided in the form of printable labels containing an RFID tag integral with the label. The RFID tags can also be affixed to or embedded in a bottom portion of the tube, as shown by RFID tag 304 in FIG. 3. Tubes can store nucleic acids for assays designed for a particular customer or for a particular assay.

Figure 4:
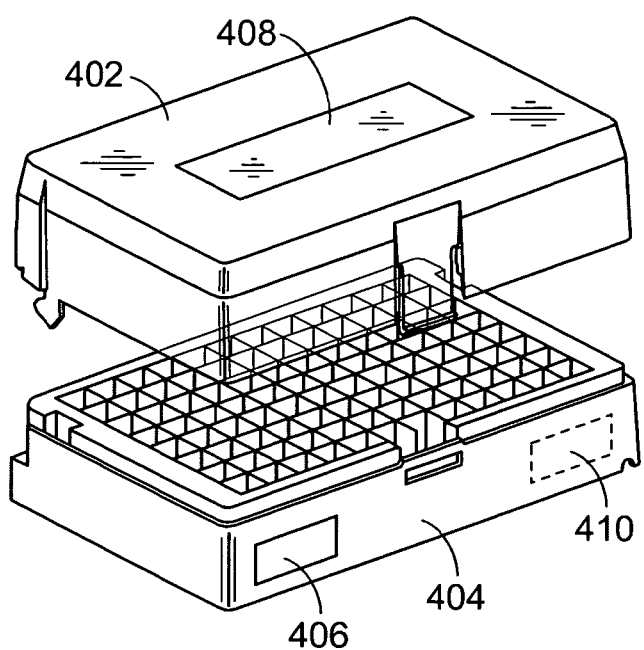
FIG. 4 illustrates an embodiment of an empty tube carrier in connection with various exemplary locations for RFID tags according to various embodiments.

FIG. 4 illustrates an embodiment of an empty tube carrier having an RFID positioned at various locations. Tube carriers such as tube carrier 400 are advantageously used to organize and transport a plurality of the tubes 300 containing biological materials. Lid 402 and tube carrier base 404 are used to protect and/or to store the tubes 300 during manufacturing, storage, transportation, and usage phases of the lifecycle of the biological materials supported by the tubes 300. In various embodiments, RFID tags in or on the tubes contain information regarding nucleic acid samples, primers, or probes contained in each of the tubes. In such embodiments information regarding the genetic sequences of the nucleic acids, for example, are stored in the RFID tags. Further, annotated information regarding the biological reagents can be stored in the RFID tags, for example, information regarding results of experiments already performed with the biological reagents.

According to various embodiments, no read/write RFID tag is directly coupled to a particular tube. Rather, the tube bears a simplified RFID tag or optical indicia that provides, for example, row and column information for the tube's position in the tube carrier 400. Then, for example, information regarding the contents of tubes can be stored in a more complex RFID tag that is affixed to or embedded into the tube carrier 400, either at the lid 402 or at the carrier base 404. Alternatively, additional information can be stored on a CDROM or other removable medium and associated with each tube, for example, based on a unique identifier on the RFID tag associated with the tube or tube carrier. The additional information can also be provided in an encrypted on-line database, as further set forth in connection with FIG. 11.

Exemplary RFID tag positions are illustrated in connection with FIG. 4. An RFID tag 408 can be applied to a surface of the lid 402. Alternatively, an RFID tag 406 can be applied to a surface of the tube carrier base 404. Still alternatively, the RFID tag 410 can be embedded into a portion of the tube carrier 400 during a manufacturing process of the tube carrier 400. It is understood that the positions of the RFID tags 406, 408, and 410 are exemplary any not inclusive and that a single or multiple RFID tags can be affixed to or embedded into various portions of the tube carrier 400 without departing from the present teachings.

Figure 5:
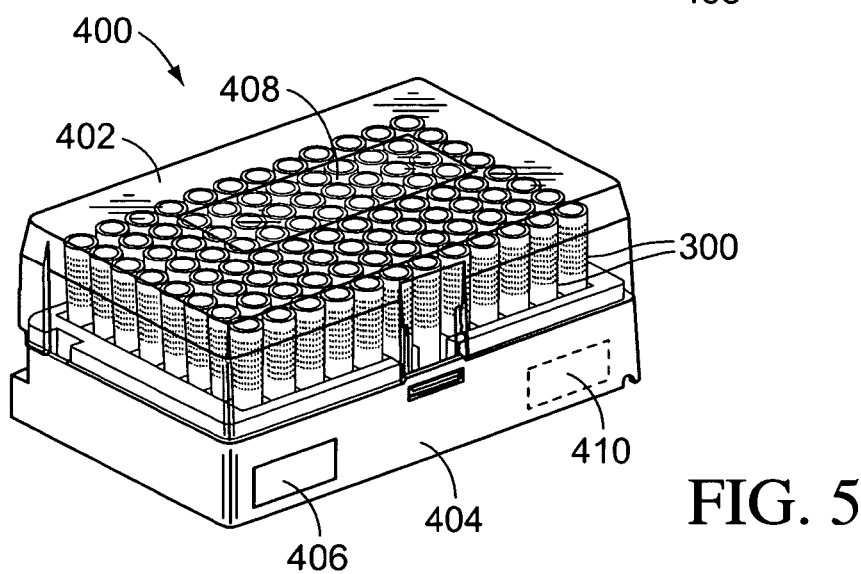
FIG. 5 illustrates a tube carrier containing a plurality of tubes in connection with various exemplary locations for RFID tags according to various embodiments.

FIG. 5 illustrates a tube carrier containing a plurality of tubes having associated individual RFID tags and at least one RFID tag on the tube carrier; In various embodiments, as shown in FIG. 5, tube carriers, such as the tube carrier 400 can contain a plurality of the tubes 300. In these various embodiments, information regarding the contents of the tubes, including, for example nucleic acid sequence information, and other annotated information is stored in an RFID tag either affixed to or embedded into each of the tubes 300 or in an RFID tag that is affixed to or embedded into the tube carrier 400.

According to various embodiments, the tube carrier 400 can contain a simplified RFID tag containing only an identifier number, which is cross-referenced to a table that contains information on the contents of particular the tubes 300 in the particular tube carrier 400. In various embodiments, the lookup table information is provided on removable, machine-readable media, such as CDROM. In various other embodiments, the lookup table information is provided in the form of a network-accessible, on-line database. In various ones of these embodiments, the lookup table information is encrypted either in an off-line CDROM-type form or in an on-line form.

According to various embodiments, authentication and/or decryption information can be stored in the RFID tag or tags on or in the tubes 300 and/or the tube carrier 400. It is understood that any type of digital authentication and/or cryptography system can be employed to provide access to and decryption for the on-line or off-line data associated with the biological contents of the carriers without departing from the scope of the present teachings.

Figure 6:
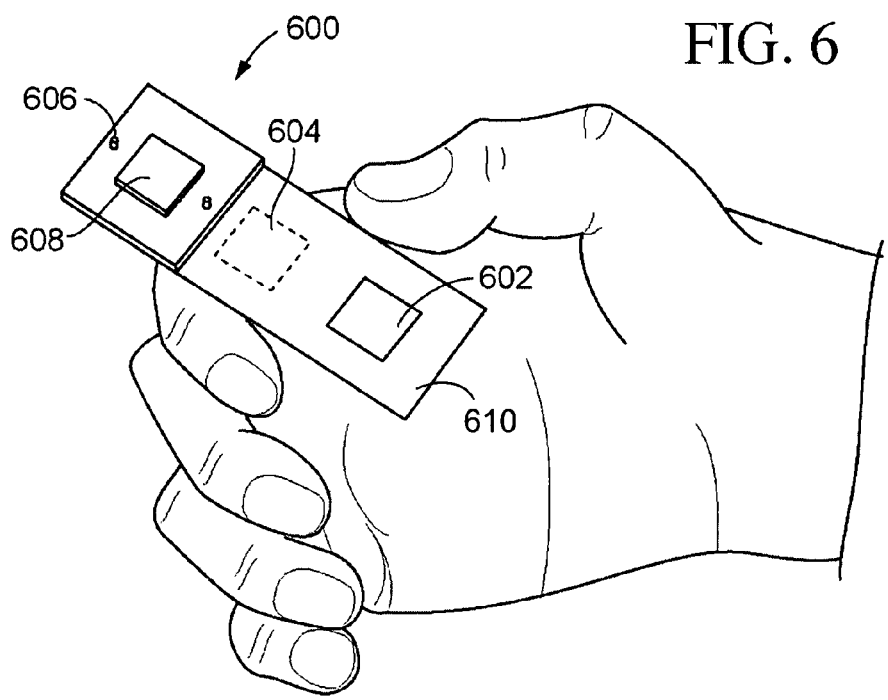
FIG. 6 illustrates an exemplary embodiment of a surface plasmon resonance (SPR) array in connection with various exemplary locations for RFID tags according to various embodiments.

FIG. 6 illustrates an exemplary embodiment of an SPR array 600 with exemplary RFID tags 604 and 602. The SPR array 600 contains ports 606 that are used to inject a biological reagent into the SPR array. In various embodiments, RFID tags 602 and 604 facilitate the association of information with biological reagents used in connection with the SPR array 600. For example, read/write RFID tag 602 can contain information regarding the biological sample injected into the SPR array. The RFID tag 602 can also be written to by an instrument that is used to detect the results of an assay conducted on the biological reagent that is injected into the SPR array. The RFID tag can further store information regarding locations and patterns of particular nucleic acid spots in the SPR array.

As described above in connection with other consumables, the RFID tags 602 and 604 can be affixed to an outer surface of the SPR array 600 (as shown with RFID tag 602) or embedded in the SPR array during manufacture (as shown with RFID 604). In various embodiments the SPR array is constructed from a standard glass slide which has a layer of gold deposited to an underside surface of the slide, and the RFID tag is adhesively applied to an upper surface 610 of the glass slide.

FIG. 7 illustrates another exemplary embodiment of a reaction plate 700 with at least one associated RFID tag. As described in connection with FIGS. 1 and 2, reaction plates such as the reaction plate 700 can be coupled to an RFID tag to facilitate the association of information with the biological contents of the reaction plate. For example, an RFID tag 702 can be applied to an exterior surface of the reaction plate 700, or an RFID tag 704 can be embedded within a portion of the reaction plate. Any reaction plate with 8, 16, 24, 48, 96 (FIG. 1), 386 (FIG. 7), etc. is contemplated by the present teachings.

Figure 8:
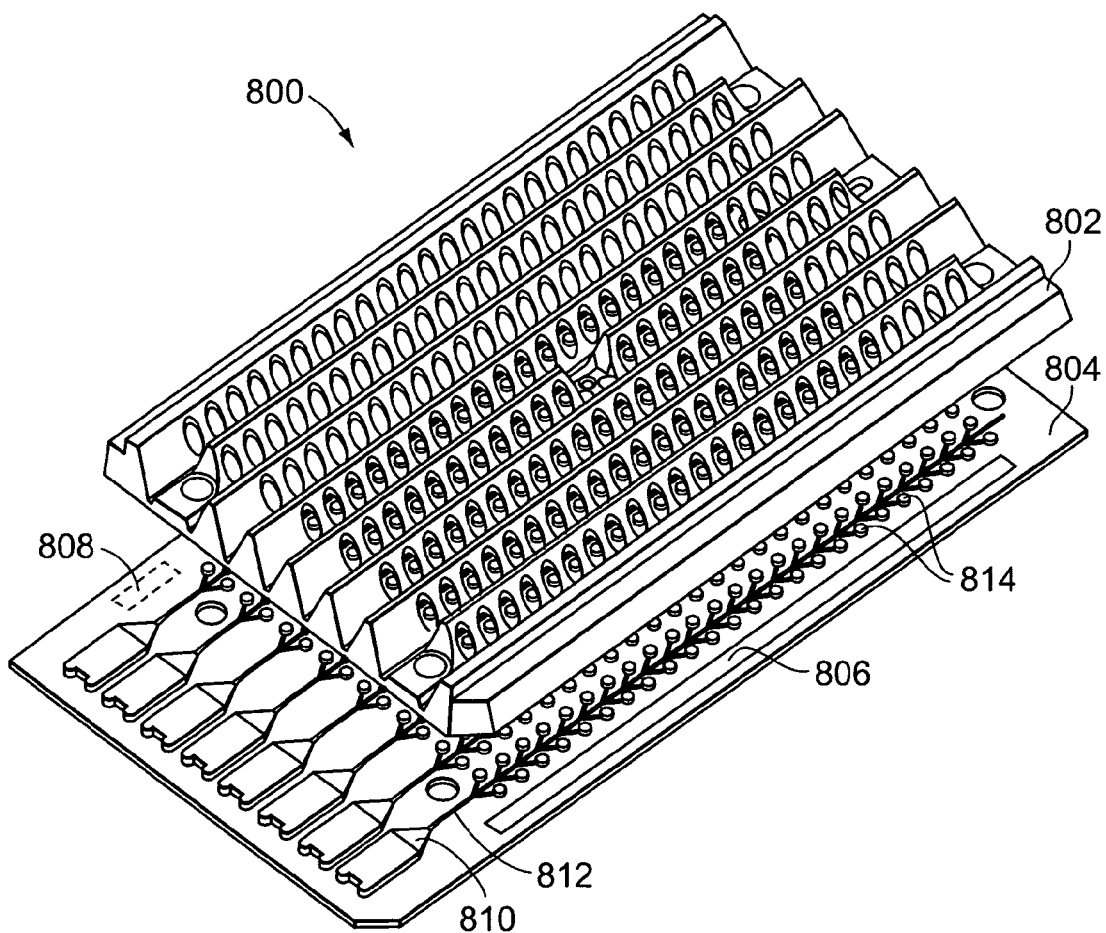
FIG. 8 illustrates an exemplary embodiment of a microfluidic card in connection with various exemplary locations for RFID tags according to various embodiments.

FIG. 8 illustrates an exemplary embodiment of a microfluidic card 800 having at least one associated RFID tag. The microfluidic card 800 provides an array containing multiple chambers 814 for testing various biological reagents on many different primer and probe sets thereby, for example, eliminating labor-intensive pipetting steps. In connection with the microfluidic card 800, biological reagents can be injected into the card via inlet ports 810 through channels 812 into the clambers 814.

According to various embodiments, information regarding the contents of the chambers and/or the contents loaded into the card can be provided. Accordingly, RFID tags consistent with the present teachings are affixed to a surface of a portion of the microfluidic card 800 for example on surface 804 as shown in connection with RFID tag 806. The RFID tag 808 is shown as being embedded into a portion of the microfluidic card 800. It is understood that the RFID tag can be affixed to or embedded in other portions of the card, such as the supporting lid portion 802, which has a plurality of apertures, through which the chambers 814 can be observed by an instrument to determine the results of an assay performed in connection with the microfluidic card 800. The RFID tag 806 can include information regarding specific assays preloaded into the microfluidic card. Further, the RFID tag 806 can include information regarding samples injected into the card, which is written to the RFID tag as the samples are being injected into the card.

Figure 9:
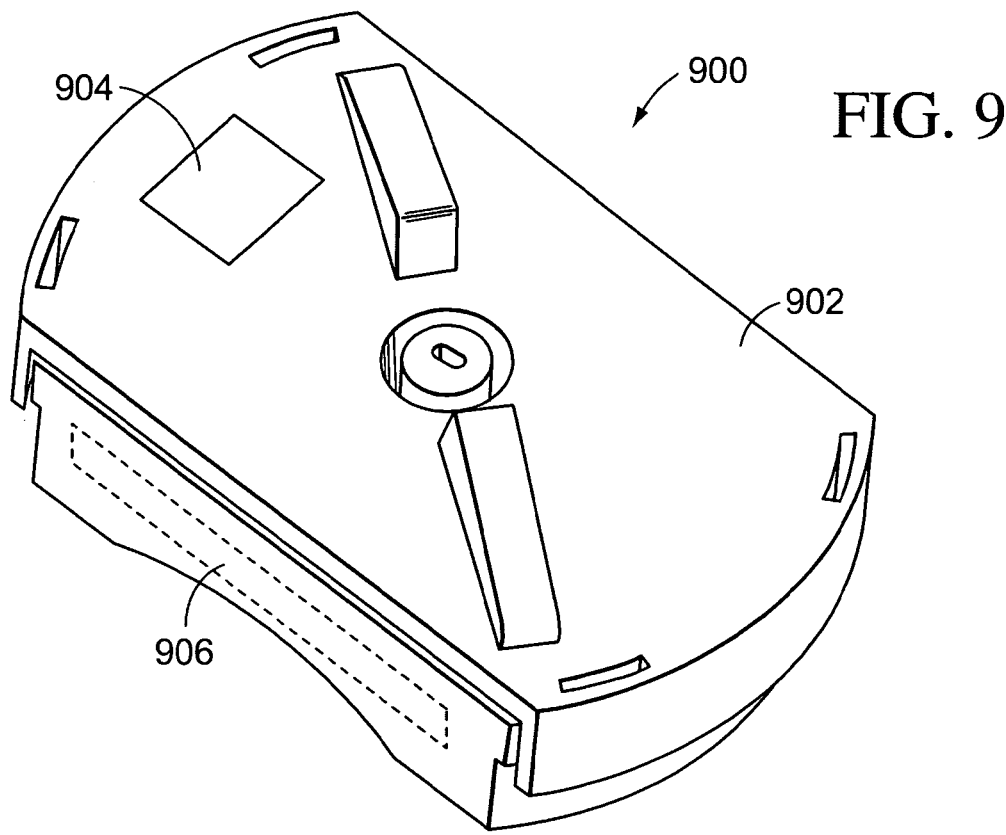
FIG. 9 illustrates an exemplary embodiment of a microarray cartridge in connection with various exemplary locations for RFID tags according to various embodiments.
Figure 10:
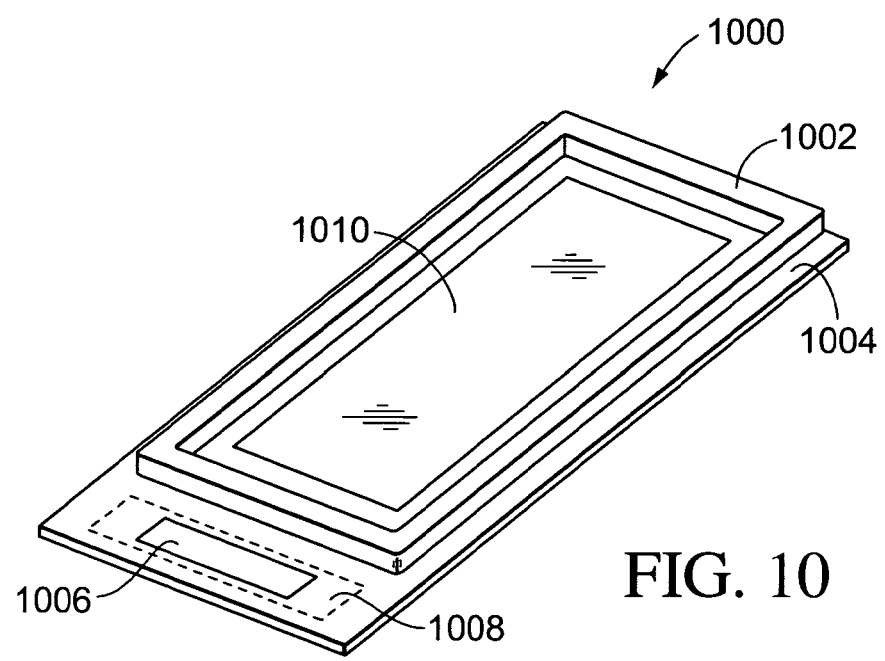
FIG. 10 illustrates an exemplary embodiment of a microarray in connection with various exemplary locations for RFID tags according to various embodiments.

FIG. 9 illustrates an exemplary embodiment of a microarray cartridge 900 with at least one associated RFID tag. The microarray cartridge 902 is provided to facilitate the protection and loading of a microarray on microarray slide 1000 as illustrated in FIG. 10. In various embodiments, the microarray cartridge 900 is substantially opaque which does not allow for the optical reading of information from the microarray slide 1000. However, consistent with the present teachings, RFID tag information can be read regarding the contents of the microarray slide 1000 even absent an optical path in the microarray cartridge 900. Additionally, information regarding the microarray contained within the microarray cartridge 900 can be stored in RFID tag 904, which can be affixed to an outer surface 902 of the microarray cartridge 900. In various embodiments, the RFID tag 906 can be embedded in a wall portion of the microarray cartridge 900.

FIG. 10 illustrates an exemplary embodiment of the microarray slide 1000 having at least one RFID tag associated with the microarray 1010. RFID tags 1006 and 1008 are shown as alternatively being embedded in substrate 1004 or as being affixed to an outer surface portion of the substrate 1004. It is understood that RFID tags can be positioned in any convenient configuration on the microarray slide 1000, including, for example along an outer periphery of the microarray slide 1000, along an outer periphery of the gasket 1002 positioned around microarray 1010 or on an underside surface of the substrate 1004 without departing from the scope of the present teachings.

According to various embodiments, information can be stored in RFID tags associated with any of the above-described consumables that can be useful, for example, in the transportation of the biological reagents. For example, in connection with the importation and/or exportation of biological reagents, biological reagent content information and country of origin information can be provided consistent with the present teachings. National customs agencies typically require the provision of such country of origin information during import and/or export of various biological reagents. It is understood that the provision of such information by way of an RFID reader interface would drastically expedite the provision to customs authorities of, for example, country of origin information for various biological reagents.

According to various embodiments, Material Safety Data Sheet (MSDS) information can be stored in the RFID tags and read at any time during the lifecycle of the biological reagent while it is contained in or supported by a carrier consistent with the present teachings.

According to various embodiments, the information stored in the RFID tags associated with the biological reagents can include traveler information that is written to the RFID tag at various stages or steps along the course of a biological assay. In various embodiments, genealogy data is read and used during the course of an assay.

According to various embodiments, biological samples or reagents that are provided in the carriers described above are licensed separately from instruments designed to operate on the biological reagents. In various embodiments the instruments are coupled to a network (see e.g. FIG. 11) that allows the instruments to communicate over public and private networks with computer systems that are operated by or on behalf of the producers and/or licensors of the biological reagents. In various embodiments, reagent licenses can provide for the use of licensed biological reagents for a particular biological analysis on only licensed instruments. In various embodiments, instrument licenses can provide for the use of licensed instruments to carry out a particular biological analysis with only licensed reagents. Accordingly, an instrument can authenticate a biological reagents based on, for example, a digital signature contained in the RFID tag associated with a particular consumable, if a particular user has a valid license. IN various embodiments, the RFID tags can also be programmed to provide a one time use such that biological reagents cannot be refilled with for use with the same authentication.

According to various embodiments, when an RFID tag is read by an instrument that has access to a data network that includes a connection to information regarding biological reagent recall information, the instrument can perform a database lookup to determine whether the biological reagent has been subject to a recall. The recall information and an optional last recall check date and/or timestamp can be written to the RFID tag. In various embodiments, a recall database lookup is performed each time before a biological reagent is utilized in an assay or other test such as, for example a clinical diagnostic procedure.

According to various embodiments, external displays are provided to display information regarding the biological reagent contents of a consumable when the biological reagent is inside of an instrument or other container, such as a refrigerator. For example when a microarray is contained within its microarray cartridge, an RFID reader can read the identification information from the microarray and display it on a human readable interface, such as a computer terminal, LCD, or other type of display.

Figure 11:
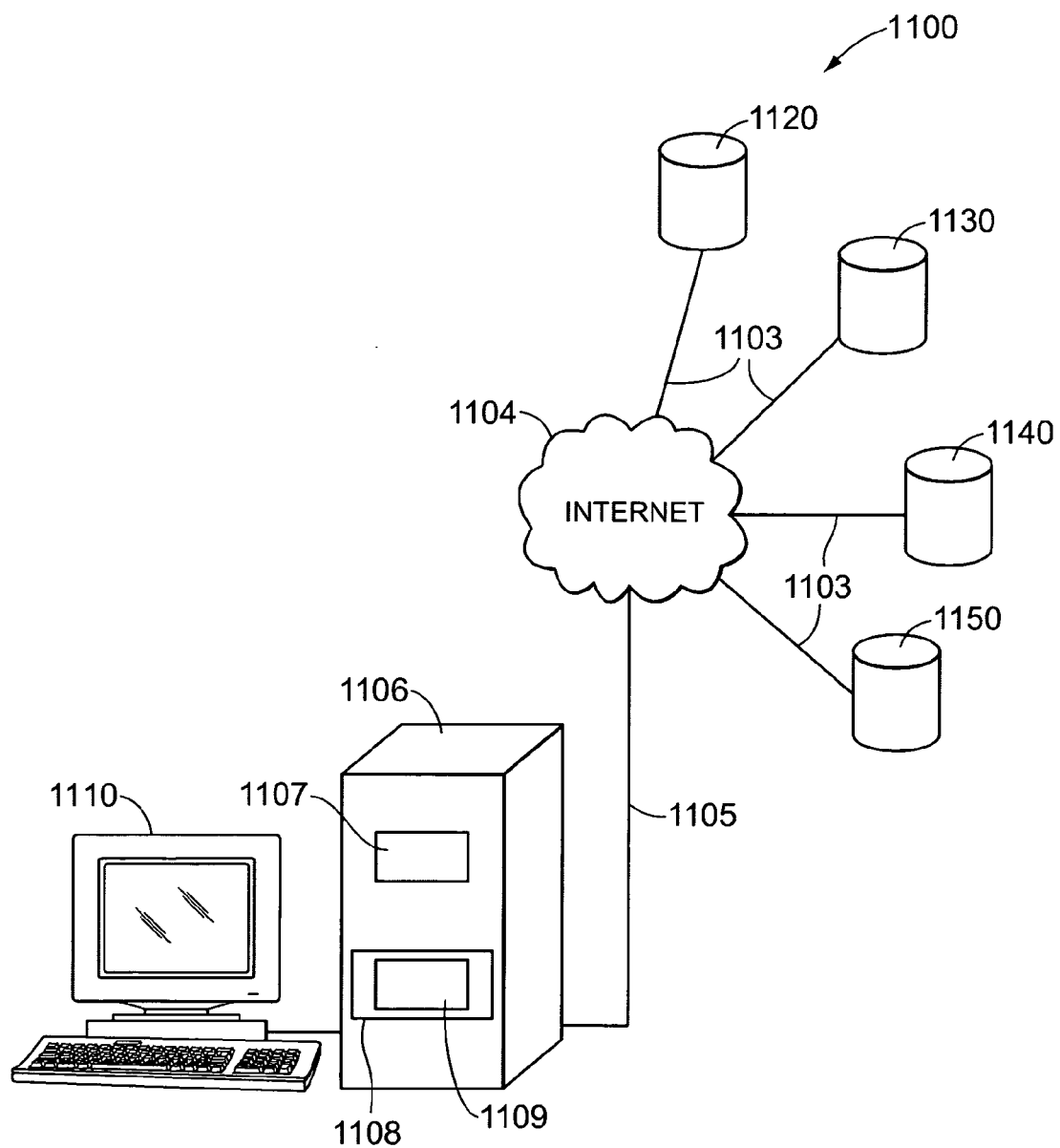
FIG. 11 illustrates an exemplary embodiment of an on-line biological instrument system according to various embodiments.

FIG. 11 illustrates an exemplary embodiment of an on-line biological instrument system 1100 consistent with the present teachings. In various embodiments, a general purpose computer 1110 serves a function of controlling an instrument 1106 as it performs operations on biological reagents supported by carriers 1108. RFID tags 1109 that are affixed on or embedded into the carriers 1108 can be read by and/or written to by the RFID reader 1107. In various embodiments, the RFID reader 1107 can read identification information from the RFID tag 1109 to identify the biological reagent being supported by the carrier 1108 at particular points in time. In various embodiments, identifying descriptions, such as the name or work number associated with the biological reagent can be displayed on the monitor of the general purpose computer 1110. In various other embodiments, the identifying descriptions can be provided on a display (not shown) that is externally connected to the instrument 1106.

Via a network connection 1105, the instrument 1106, and/or the general purpose computer 1110 can be connected to a public or private network, such as internet 1104. It is understood that any networking technology can be employed without departing from the present teachings, including wired and wireless networking technologies. It is also understood that, in various embodiments, the network connection associated with the instrument 1106 can emanate from the instrument 1106 as shown or from the general purpose computer 1110.

By employing a network connection, the instrument 1106 and/or its associated general purpose computer 1110 can remotely access databases 1120, 1130, 1140, and 1150 via remote network connections 1103. In various embodiments, information contained in the databases 1120, 1130, 1140, and 1150 can be written to the RFID tag 1209 as set forth below in connection with FIG. 12. In various embodiments, the database 1120 can include identification information. In various embodiments, the database 1130 can include supplemental information, such as annotated information regarding a biological reagent. In various embodiments, the database 1140, can include rights information, which as set forth above can be used to authenticate or validate the biological reagent and/or determine the validity of licenses associated with the biological reagent. In various embodiments, databases 1140 can include information used to check for any product recalls associated with the biological reagent. In various embodiments, the database 1150 can contain information regarding instrument operations. In various embodiments, connections to the databases are encrypted for privacy. In various embodiments, the contents of the databases 1120, 1130, 1140, and 1150 are encrypted for confidentiality and to facilitate access control to the information contained in the databases 1120, 1130, 1140, and 1150.

According to various embodiments, the instrument 1106 includes instrument hardware, instrument firmware, instrument data acquisition and control software, and method or module data. In various embodiments, the instrument hardware includes electronic control and data processing circuitry, such as a microprocessor or microcontroller, memory, and non-volatile storage. In various embodiments, the instrument hardware also includes physical devices to manipulate biological reagents such as robotics and sample pumps. In various embodiments, the instrument firmware includes low-level, computer-readable instructions for carrying out basic operations in connection with the instrument hardware. In various embodiments, the instrument firmware includes microprocessor instructions for initializing operations on a microprocessor in the instrument hardware.

According to various embodiments, the instrument data acquisition and control software is higher-level software that interfaces with the instrument firmware to control the instrument hardware for more specific operations such as operating a charge coupled device (CCD) to acquire visual luminescence information regarding a particular biological analysis. In various embodiments the data acquisition and control software includes a software-implemented state machine providing, for example, the following states: (i) idle; (ii) running; (iii) paused; and (iv) error. In various embodiments, when the state machine is in the idle state, it can receive an instruction from the general purpose machine 1110 to perform a particular data acquisition or instrument control operation. In various embodiments, the general purpose computer 1110 opens a TCP/IP socket connection to the instrument 1106, determines whether the instrument 1106 is in the idle state and then begins transmitting instructions and/or parameters. In various embodiments, an encrypted TCP/IP connection is established, using, for example, the SSH protocol. The instructions and/or parameters can be in the form of ASCII encoded, human readable module and/or method information that defines the behavior of the biological instrument. In various embodiments, the modules and/or methods are stored in the form of ASCII text files. In various embodiments, the general purpose computer 1110 uses the FTP protocol to transfer the ASCII text files to the instrument 1106. In various other embodiments the method and/or module information is stored in and read from the RFID tag 1109. The method and/or module information can be stored in the form of an ASCII text file in the RFID tag 1109, but it is understood that the information can be represented in other data formats without departing from the present teachings. In various embodiments, methods and module information is stored in a relational database, such as those available from the Oracle Corporation of Redwood Shores, Calif.

According to various embodiments, the module, macro, and/or method information includes parameters that can be used by the instrument data acquisition and control software to perform specific data acquisition and instrument control operations. In various embodiments, the method and/or module information contains sequences of operations to be performed by the instrument or control parameters for use in connection with the data acquisition or control software.

Figure 12:
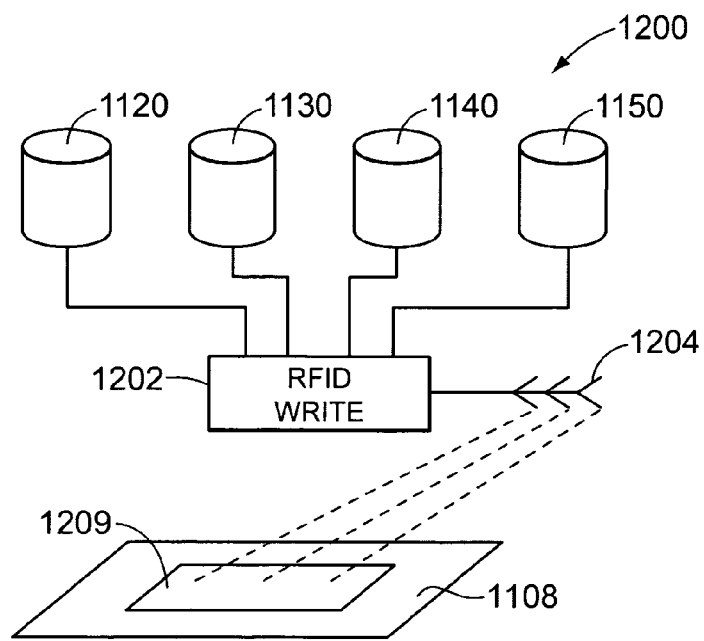
FIG. 12 illustrates an exemplary embodiment of an RFID writing apparatus according to various embodiments.

FIG. 12 illustrates an exemplary embodiment of an RFID writing apparatus 1200 consistent with the present teachings. RFID carrier 1108 is shown with an associated read/write capable RFID tag 1209. In various embodiments, an RFID reader 1202, having RFID read and write capabilities and antenna 1204, is coupled to the databases 1120, 1130, 1140, and 1150 including identification, supplemental, rights, and instrument operation information respectively. In this configuration any combination of identification, supplemental, rights, and/or instrument operation information can be written to the RFID tag 1209 consistent with the present teachings.

Figure 13:
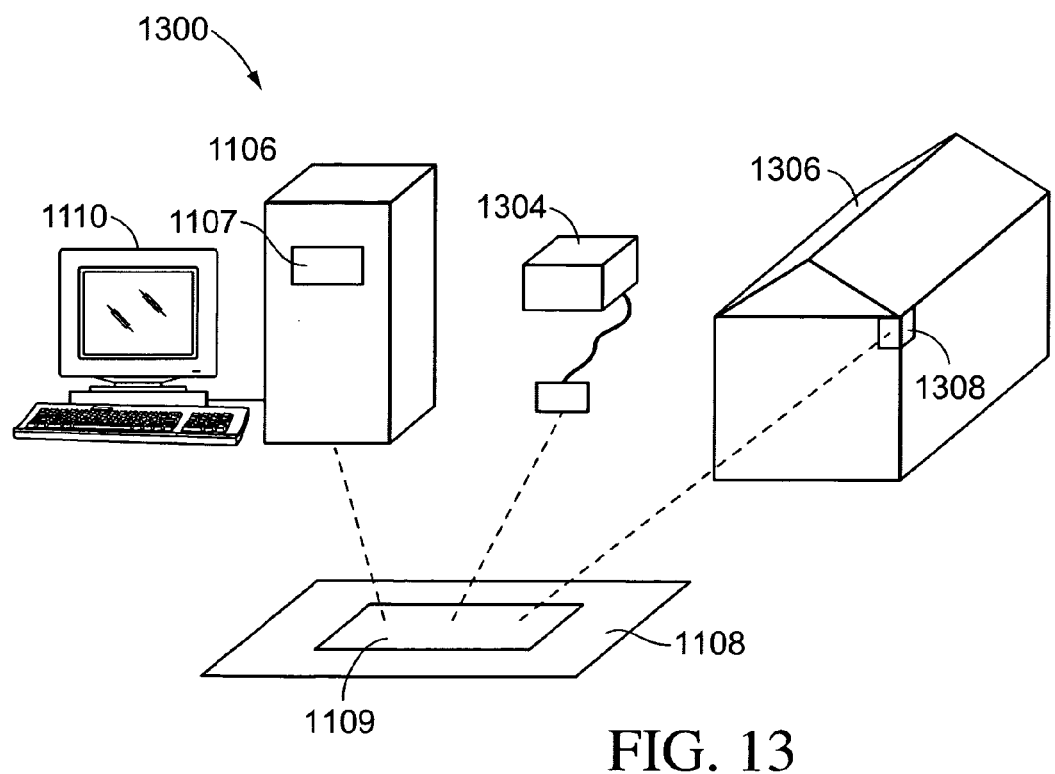
FIG. 13 illustrates an exemplary embodiment of RFID tag tracking systems according to various embodiments.

FIG. 13 illustrates an exemplary embodiment of RFID tag tracking systems 1300 consistent with the present teachings. A warehouse 1306 or manufacturing facility includes one or more RFID readers 1308, which can be used to read RFID tags on carriers such as carrier 1108 as the carriers move throughout the warehouse 1306 or manufacturing facility. The RFID readers 1308 can be used for inventory control and to provide real-time product location information. In various embodiments an instrument 1106 can perform operations on a biological reagent being supported by the carrier 1108, while the RFID reader 1308 provides general location information regarding a location of the carrier 1108. Moreover, the external RFID reader 1304 can read from and/or write information into the RFID tag 1109. In various embodiments, external, hand-held RFID readers such as the RFID reader 1304 can be used to write to or read information from the RFID tags 1109. According to various embodiments, obtaining the real-time physical location coordinates of a carrier can be achieved by receiving GPS coordinates from a GPS receiver physically coupled to the carrier.

The section headings used herein are for organizational purposes only and are not to be construed as limiting the subject matter described in any way.

All literature and similar materials cited in this application, including but not limited to, patents, patent applications, articles, books, treatises, and internet web pages, regardless of the format of such literature and similar materials, are expressly incorporated by reference in their entirety for any purpose.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed:

1. A biological device comprising:
    a housing;
    at least one opening in the housing, wherein the at least one opening is configured to receive at least one carrier containing a biological reagent and having an RFID tag affixed thereto or embedded therein;
    a processor; and
    a memory encoded with instructions executable by the processor, wherein the instructions include instructions for:
        interrogating the RFID tag for identification information, and
        controlling the biological device based on the identification information,
    wherein controlling the biological device includes using the identification information to restrict use of the biological device.

2. The device of claim 1, wherein the identification information includes authentication information.

3. The device of claim 1, comprising an RFID reader coupled to the housing and configured to interrogate the RFID tag.

4. The device of claim 1, wherein restricting the use of the biological device is restricting the number of times the biological reagent is used.

5. The device of claim 4, wherein restricting the use of the biological device is restricting consumable use to a one time use.

6. The device of claim 1, wherein the processor is configured to communicate over a network with a database.

7. The device of claim 6, wherein the database includes information to validate the identification information.

8. The device of claim 6, wherein the database includes information regarding instrument operation.

9. The device of claim 1, wherein the controlling comprises comparing the identification information to a look-up table.

10. The device of claim 1, wherein the device comprises a display.

11. The device of claim 10, wherein the display is configured to display a message to a user based on the identification information.

12. The device of claim 1, wherein the device is a sequencer.

13. A biological device comprising:
    a housing;
    an RFID reader, wherein the RFID reader is capable of interrogating an RFID tag associated with a reagent carrier; and
    a processor capable of processing information from the RFID reader,
    wherein the processor is capable of determining from the processed information whether the reagent carrier is authorized for use.

14. The device of claim 13, wherein the information is an unique identifier associated with the RFID tag.

15. The device of claim 14, wherein the device includes a network connection configured to connect to a remote database.

16. The device of claim 15, wherein the remote database is a database of unique identifiers associated with RFID tags.

17. The device of claim 15, wherein the device includes a barcode reader.

18. The device of claim 13, wherein the device includes a detector configured to monitor a biological analysis.

19. The device of claim 18, wherein the biological analysis is sequencing.

20. The device of claim 18, wherein the biological analysis is amplification a nucleic acid sequence.

* * * * *